(12) United States Patent
Hariharan et al.

(10) Patent No.: US 12,125,172 B2
(45) Date of Patent: Oct. 22, 2024

(54) ADJUSTING A PARAMETER FOR NOISE SUPPRESSION IN X-RAY IMAGING

(71) Applicant: Siemens Healthcare GmbH, Erlangen (DE)

(72) Inventors: Sai Gokul Hariharan, Forchheim (DE); Christian Kaethner, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 441 days.

(21) Appl. No.: 17/592,699

(22) Filed: Feb. 4, 2022

(65) Prior Publication Data

US 2022/0270214 A1 Aug. 25, 2022

(30) Foreign Application Priority Data

Feb. 24, 2021 (DE) .................. 10 2021 201 748.7

(51) Int. Cl.
*G06T 5/70* (2024.01)
*G06T 7/00* (2017.01)

(52) U.S. Cl.
CPC .............. *G06T 5/70* (2024.01); *G06T 7/0012* (2013.01); *G06T 2207/10116* (2013.01)

(58) Field of Classification Search
CPC ............. G06T 5/70; G06T 2207/30004; G06T 2207/10116; G06T 2207/20192; G06T 7/0012; G06T 2207/10144; G06T 5/00; G06T 2207/30168; G06T 7/136; A61B 6/5258; A61B 6/54; A61B 6/5211; A61B 2090/376; A61B 8/5207; A61B 8/5269; A61B 6/5217; H04N 5/32; H04N 25/60;
(Continued)

(56) References Cited

U.S. PATENT DOCUMENTS 7,912,316 B2 * 3/2011 Sasada ..................... G06T 5/75
348/607
7,970,098 B2 * 6/2011 Haras ................... A61B 6/4441
378/16
(Continued)

FOREIGN PATENT DOCUMENTS

JP 2005021456 A * 1/2005

OTHER PUBLICATIONS

Machine translation of JP 2005021456A obtained from google patents (Year: 2005).*
(Continued)

*Primary Examiner* — Aaron W Carter
*Assistant Examiner* — Courtney Joan Nelson
(74) *Attorney, Agent, or Firm* — Lempia Summerfield Katz LLC (57) ABSTRACT

An object of this disclosure is to allow dose-specific alteration of the noise suppression in X-ray images, wherein the image quality may change only below the threshold of perceptibility. To achieve this, a method is provided for adjusting a parameter for noise suppression in X-ray imaging, in which quality functions are determined in relation to a variation of a noise suppression parameter. Maximum values of the variation are set for each quality function based on a threshold value. The variability of the noise suppression parameter may be limited according to the X-ray dose up to the set maximum value.

16 Claims, 4 Drawing Sheets

(58) Field of Classification Search
CPC .... G06V 10/30; G06V 2201/03; G16H 30/20; G16H 30/40
See application file for complete search history.

(56) References Cited

U.S. PATENT DOCUMENTS 8,824,753 B2 * 9/2014 Souza ..................... G06T 5/20
382/128
10,546,367 B2 * 1/2020 Reusch ................ G06T 1/0007

OTHER PUBLICATIONS

Hariharan et al.: Learning-Based X-Ray Image Denoising Utilizing Model-Based Image Simulations, MICCAI 2019, 549-557, 2019.
Yang, Xiaoli et al: "TV-based conjugate gradient method and discrete L-curve for few-view CT reconstruction of X-ray in vivo data"; Optics express; vol. 23, No. 5, pp. 5368-5387, 2015.

* cited by examiner

ADJUSTING A PARAMETER FOR NOISE SUPPRESSION IN X-RAY IMAGING

The present patent document claims the benefit of German Patent Application No. 10 2021 201 748.7, filed Feb. 24, 2021, which is hereby incorporated by reference in its entirety.

TECHNICAL FIELD

The present disclosure relates to a method for adjusting a parameter for noise suppression in X-ray imaging, wherein a baseline parameter value for noise suppression is provided. The present disclosure also relates to an X-ray imaging method that includes the adjustment method, and to a computer program, to an electronically readable data storage medium, to a control apparatus, and to an X-ray imaging apparatus.

BACKGROUND

Noise suppression in X-ray images is an integral part of X-ray based medical methods, in particular those carried out in the low-dose range. Although conventional noise-suppression techniques may deliver satisfactory results for standard doses, the suppression performance may be inadequate at low doses. This gap in performance has recently been closed by the introduction of learning-based noise-suppression methods, for instance, based on simulated pairs of noisy images in the training phase. Such a method is disclosed, for example, in the following article: S. G. Hariharan, C. Kaethner et al.: "Learning-Based X-Ray Image Denoising Utilizing Model-Based Image Simulations", MICCAI 2019, pages 549 to 557.

Although there are options for altering the degree of noise suppression when using learning-based noise-suppression techniques, it is still a challenge to provide a constant image quality impression. In particular, it is necessary to avoid artifacts and loss of sharpness when the noise suppression is altered, especially if a pre-trained algorithm is being applied over a number of dose levels.

SUMMARY AND DESCRIPTION

The object of the present disclosure is therefore to be able to provide in X-ray imaging, an image quality that is as constant as possible despite variability in the noise suppression.

The scope of the present disclosure is defined solely by the appended claims and is not affected to any degree by the statements within this summary. The present embodiments may obviate one or more of the drawbacks or limitations in the related art.

The present disclosure provides a method for adjusting a parameter for noise suppression in X-ray imaging. X-ray imaging of this type may be used not just in the medical sector but also for industrial applications. For instance, applications arise in the specific examination of organs of a patient but also in the non-destructive analysis of technical objects. The X-ray images accordingly obtained may be noisy, with the result that it is difficult for the user to discern the required details. Appropriate noise suppression is therefore applied to the X-ray images. This may be done by using known noise suppression algorithms or noise suppression filters. These algorithms or filters may have one or more parameters which may be varied, e.g., are adjustable.

In a first act of the method, a baseline parameter value for noise suppression is provided. For the noise suppression, a baseline parameter value is thus provided as an initial value or basis for the filtering. The provision may be performed in a permanent storage device, for example. It is also possible, however, for the provision to be made by a lookup table, for example. If applicable, the provision may also include further method acts, the result of which is the desired baseline parameter value, for instance computer-implemented learning.

In addition, for each of a plurality of X-ray doses, a quality function of a quality metric of an X-ray image is determined in relation to a variation of the parameter for noise suppression with respect to the baseline parameter value. The quality metric may also be called a quality measure or measure of quality. In particular, this quality metric may relate to structural properties of the image or to signal-to-noise ratios. The quality metric may specifically be a relative quantity with respect to a reference image. The reference image may be obtained by optimization methods, automated learning methods, and the like.

The quality functions may be determined automatically. This involves analyzing an effect of a change to the parameter for noise suppression. A specific example is investigating the change to the size of a filter. The quality function then represents the quality metric or measure of quality in relation to a change to the parameter. In other words, the quality metric is plotted against the parameter variation. An example of a function value may be the quality of the X-ray image when the parameter for noise suppression is varied by, for example, 60 percent.

A plurality of quality functions is determined for a plurality of X-ray doses. This results in a set of functions having the X-ray dose as an additional parameter. A quality function may also be the result of one or more quality subfunctions, which are combined with one another, if applicable in a weighted manner. Such a quality subfunction reflects, for example, an aforementioned quality metric and may serve as a preliminary stage for creating the quality function.

In addition, a maximum value of the variation of the parameter for noise suppression with respect to the baseline parameter value is set for each quality function, wherein a quality value associated with the particular maximum value in accordance with the particular quality function is less than or equal to a specified threshold value. Thus, for instance, the aim is to set the maximum extent by which the parameter for noise suppression may be varied. The image quality may be one criterion for this. For example, the maximum value may be set such that it is still just possible not to perceive any artifacts. Alternatively, the maximum value may also be set such that the viewer still cannot perceive any blurring of the X-ray image. A maximum value may be set for each quality function, e.g., for each X-ray dose. In particular, it may be helpful to set the maximum value in specified steps. For example, it is favorable to set the maximum value in steps of 5 or 10 percent of a variation with respect to the baseline parameter value. It is also possible for the maximum value to lie below the baseline parameter value. If, in this case, the maximum value limits the adjustability, the baseline parameter value lies outside the selectable adjustment range.

The maximum value may be found by a specified threshold value. The threshold value constitutes, for example, a maximum permissible variation with respect to a reference image. For instance, the threshold value may be chosen to be 50 percent for a coefficient of variation relating to a SSIM value (structural similarity value). That point of the quality function at which the quality function crosses the threshold value may then be chosen as the maximum value. Specifically, however, the maximum value may also be that value for which the quality metric still lies below the threshold value for an integer multiple of 5 or 10 percent of the range of variation of the parameter for noise suppression. Threshold values may be defined in preliminary studies with users for assessing the noise suppression or the image quality, or else in specifications or recommendations based on a trained function.

Finally, a variability of the parameter for noise suppression according to the X-ray dose is limited up to the corresponding maximum value. This means, for example, that when adjusting the noise suppression, the user may vary the parameter only up to the associated maximum value for a particular X-ray dose. In addition, for example, the X-ray imaging apparatus does not allow the parameter to be varied. This provides that a certain level of image quality is maintained even when the user personally adjusts or varies the parameter for noise suppression. This limiting of the variability may be performed by software or even by hardware. For example, there is no further change in the parameter even if an adjusting wheel or suchlike continues to be turned/adjusted. Alternatively, however, an end stop for an adjusting wheel may also be modified according to the X-ray dose, in order that the parameter may be varied by the adjusting wheel only as far as the given end stop.

Alternatively, an assessment of a present variation of the parameter for noise suppression with respect to the particular maximum value may be performed according to the X-ray dose. This means that, in principle, the user may adjust the parameter for noise suppression regardless of the maximum value. If, however, the maximum value is exceeded, for example, the selected or adjusted parameter may be displayed in a different color, for instance red. Below the maximum value, the selected parameter is displayed green, for example. The user is thereby given an immediate indication of the image quality, because above the maximum value, associated artifacts or blurring, for example, may be expected. The current change in the parameter is thus assessed visually in the present example. It is also possible, however, for the assessment to be made in a different manner, for instance, audibly or haptically. For instance, a warning sound may be emitted if the parameter is adjusted beyond the maximum value. Equally, a vibration may signal that adjustment of the parameter is beyond the maximum value.

The particular advantage of the adjustment method as described above consists in that by using the maximum values, the quality of the X-ray image may be kept constant, for instance in terms of perceptibility. Hence, changes to the parameter for noise suppression below the maximum value may not be perceptible. Only parameter changes or adjustments beyond the maximum value lead to visible artifacts or blurring.

In one embodiment, the quality metric is a structural similarity metric or a noise ratio metric. For example, the structural similarity metric may be the SSIM (Structural Similarity Index Method), or a value based thereon. For instance, a coefficient of variation based on the SSIM may thus be used as the structural similarity metric. Alternatively, the quality metric or measure of quality may be a noise ratio metric, for example the PSNR (peak signal-to-noise ratio). In this case, the maximum noise peaks serve as the measure of quality.

In a further embodiment, the parameter for noise suppression is a filter parameter of a noise suppression algorithm. One such filter parameter may be the size of the filter, for example. For instance, a 3×3 or 4×4 filter may be used instead of a 2×2 filter. Another filter parameter may relate to the weighting of individual pixels. A filter may also be a distribution function, for instance a normal distribution. This may then be adjusted accordingly, for instance, in the case of the normal distribution, via the parameter values of mean and standard deviation. In particular, these filters may also be related to the imaging system or may model or simulate part of the processing chain. A huge variety of filter functions may be implemented by the filter parameters.

In a particular embodiment, the plurality of X-ray doses may include a specified standard dose and one or more fractions of the standard dose, in particular between 50 percent and 10 percent of the standard dose. For instance, a quality function may be determined for the single standard dose SD (100 percent SD). In addition, for example, a quality function is determined for 50 percent SD, 30 percent SD, and 15 percent SD. In another example, in addition to the quality function for the standard dose 100 percent SD, just a single further quality function is obtained, for instance for 20 percent SD. In yet another example, three quality functions may be used, for instance for 100 percent SD, 50 percent SD and 10 percent SD. The number of fractions of the standard dose that are to be used, and obtaining a corresponding number of quality functions, may be matched to the types of objects under examination. Additionally, or alternatively, the calculations may be performed only for certain fractions, and the maximum values determined accordingly for these. For other fractions which lie between the selected fractions, a result, (e.g., the maximum values), may accordingly be determined via interpolation.

It may be provided as a further option that the threshold value is specified according to a type of an object to which the X-ray imaging is applied. For instance, the threshold value in a medical X-ray examination may be selected according to the type of organ under examination. Thus, for example, the threshold value, below which there is no, or practically no, perceptible change in image quality may differ for a liver under examination compared with bones under examination. Yet another threshold value may be favorable for depicting vessels. Also, when X-ray imaging is used for industrial fault investigation, the threshold value may be adapted to the object type. For instance, it is definitely necessary to select the threshold value for examining turbine blades to be different from that for examining blades of a wind farm.

Furthermore, it may also be provided that the threshold value is specified in a custom manner. This means that the threshold value may be entered specifically for a user, for example. An interface is accordingly provided, by which the user may select a personal threshold value. In a specific example, a radiologist selects a different threshold value from his colleague. For instance, it is possible that a radiologist may still easily discern structures being sought in an X-ray image even when the image exhibits strong artifacts. This may be advantageous for the patient if they are thereby exposed to a lower level of radiation.

According to a further advantageous embodiment, each maximum value for limiting the adjustability, or for assessing the present adjustment, of the parameter for noise suppression is used with regard to mathematically positive values, and a corresponding minimum value of the same magnitude for limiting the adjustability, or for assessing the present adjustment, of the parameter for noise suppression is used with regard to mathematically negative values. For example, the parameter for noise suppression may be varied from the baseline parameter value in a positive direction and in a negative direction. For instance, a filter which is a distribution function may be made correspondingly wider (e.g., positive direction) or narrower (e.g., negative direction). In the positive direction, the maximum value sets the limit or the assessment. In the negative direction, the minimum value sets the limit or the assessment. Maximum value and minimum value may be at a same distance from the baseline parameter value. In principle, however, the distances of the two extreme values from the baseline parameter value may also be different, in which case a separate calculation may be performed.

In a particular embodiment of the method, providing the baseline parameter value for noise suppression is based on computer-implemented learning. Thus in the present example, the baseline parameter value is a learning-optimized parameter value. The baseline adjustment for the X-ray imaging is hence based on an automated learning process and constitutes an optimized adjustment. Starting from this optimized adjustment, the user may then vary the parameter for noise suppression, for instance because of the object type under examination or for reasons of personal preference. Regardless of computer-implemented learning (e.g., machine learning), however, the method may also be applied to a plurality of different parameters for noise suppression. In this case, the starting point is simply a plurality of baseline parameter values, which may be varied in a corresponding manner.

The disclosure also provides an X-ray imaging method that includes a method for adjusting a parameter for noise suppression in X-ray imaging, as was described above. Thus, in this X-ray imaging method, the selected adjustment is used in order to obtain correspondingly denoised X-ray images. The denoising or noise suppression is performed according to the selected parameter(s).

In addition, a computer program is provided, which may be loaded directly into a memory of a control device of an X-ray imaging apparatus. The computer program has program code in order to perform the acts of the aforementioned method when the computer program is executed in the control device of the X-ray imaging apparatus. The present disclosure may also assume the form of a computer program product, which includes program modules that may be accessed by a computer-usable or computer-readable medium, which stores program code for use by, or in conjunction with, one or more computers, processors or a command execution system. For the purposes of this description, a computer-usable or computer-readable medium may be any facility that may contain, store, communicate, forward or transport the program for use by, or in conjunction with, the command execution system. The medium may be an electronic, magnetic, optical, electromagnetic, infrared, or semiconductor system (or a facility or an apparatus) or may be a propagation medium in and of itself as signal carrier. The medium may be a semiconductor memory or solid-state memory, a magnetic tape, a replaceable computer diskette, a direct access memory (RAM), a read-only memory (ROM), a rigid magnetic disk, and an optical disk such as a compact disc read-only memory (CD-ROM), compact disc read/write and DVD. Both the processors and the program code for implementing the individual aspects of the technology may be centralized or distributed (or a combination thereof).

Although the present disclosure has been described in detail with reference to certain embodiments, it is not restricted to these embodiments. Regarding the present disclosure, numerous modifications and variations are conceivable to a person skilled in the art. Therefore, the scope of the present disclosure is defined by the following claims and not by the prior description. Any changes, modifications and variations that lie within the sense and within the range of equivalence of the claims shall be deemed within the scope of protection. All advantageous embodiments claimed in the method claims may also be applied to the system claims/apparatus claims.

Thus specifically, an electronically readable data storage medium with electronically readable control information stored thereon is also provided, which control information includes at least one aforementioned computer program and is configured to perform an above-described method when the data storage medium is used in a control device of an X-ray imaging apparatus.

The above-mentioned object is achieved by a control apparatus for adjusting a parameter for noise suppression in X-ray imaging. The control apparatus includes a storage device for providing a baseline parameter value for noise suppression. The control apparatus further includes a processing device for determining for each of a plurality of X-ray doses, a quality function of a quality metric of an X-ray image in relation to a variation of the parameter for noise suppression with respect to the baseline parameter value. The control apparatus further includes an adjustment device for setting for each quality function a maximum value of the variation of the parameter for noise suppression, wherein a quality value associated with the particular maximum value in accordance with the particular quality function is less than or equal to a specifiable threshold value. The control apparatus further includes a control element for limiting an adjustability of the parameter for noise suppression according to the X-ray dose up to the corresponding maximum value, or an evaluation device for assessing a present adjustment of the parameter for noise suppression with respect to the corresponding maximum value according to the X-ray dose.

The storage device of the control apparatus thus stores and provides for further data processing, one or more baseline parameter values. The processing device, which has a processor, for instance, determines the respective quality functions, and for this purpose has a data connection not only to the storage device but also, if applicable, to other storage devices that store X-ray images having different noise suppression values. The adjustment device is also connected to the processing device in order to be able to achieve the necessary change to the parameter. The adjustment device may operate on the basis of software and/or hardware. Finally, a control element is provided that is in turn operatively connected to the adjustment device. This control element uses hardware or software to provide the limiting of the adjustability. Alternatively, an evaluation device may also be provided, which is likewise operatively connected to the adjustment device in order to achieve the assessment of the present adjustment by suitable hardware or software.

Finally, an X-ray imaging apparatus or device is provided that has the aforementioned control apparatus. Thus, the X-ray imaging may be realized by noise suppression that is adjustable by the control apparatus.

BRIEF DESCRIPTION OF THE DRAWINGS

The present disclosure is now explained in more detail with reference to the accompanying drawings, in which.

DETAILED DESCRIPTION

The present disclosure is based on the idea of overcoming the current technical limitations in particular of the learning-based noise-suppression method by providing dose-specific alteration ranges within which a constant image quality may be provided. The amount of noise suppression may be varied within the adjustment range, for instance on the basis of a user preference or in order to adapt to a particular situation, without the image quality suffering as a result. Since the magnitude of the noise, and also, to a certain extent, also the properties of the noise, depend heavily on the selected X-ray dose, it is crucial that the adjustment of the noise suppression is dose-dependent, in particular because artifacts or image degradations such as loss of sharpness are routinely produced with noise suppression at very low X-ray doses.

Figure 1:
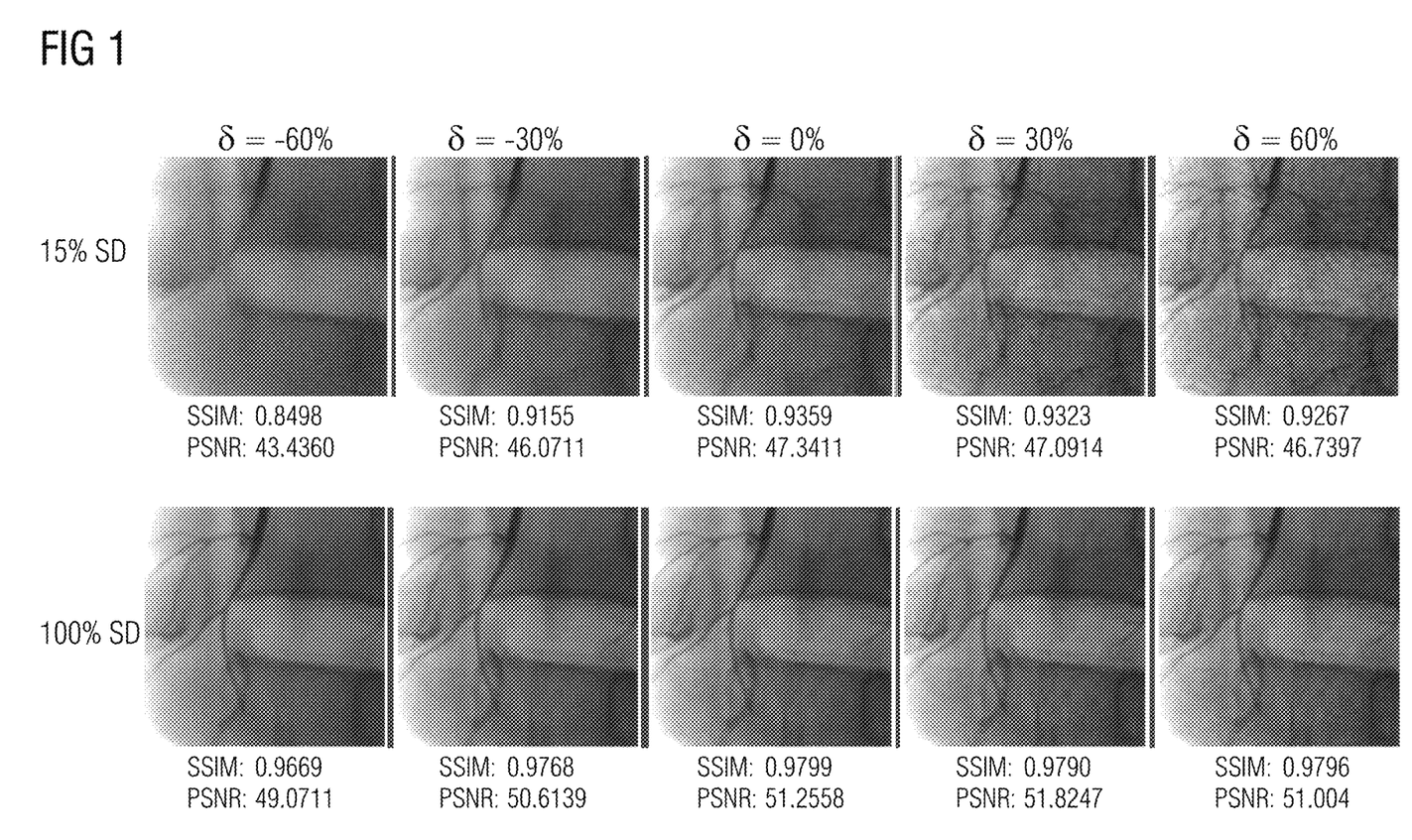
FIG. 1 depicts ten examples of X-ray images for visualizing different noise suppressions.

FIG. 1 shows an example of dose-dependent effects of an adjustable noise-suppression method. FIG. 1 shows ten X-ray images in two rows. The bottom row was acquired at a standard X-ray dose, (100 percent SD). The top row was acquired at a reduced dose of 15 percent of the standard dose, (15 percent SD). In the two rows of images, a system parameter δ for the noise suppression or the noise suppression algorithm is varied or given a different adjustment. A desired value for the system parameter for noise suppression is determined by computer-implemented learning, for instance, and constitutes a baseline parameter value. FIG. 1 shows this baseline parameter value applied in the central column where δ=0 percent. Here, there is no deviation from the baseline parameter value. FIG. 1 shows to the right and left, X-ray images for which the parameter value deviates from the baseline parameter value by +/−30 percent and +/−60 percent respectively. The effect of the parameter change is clearly visible in the X-ray images in the top row at 15 percent SD. Large negative deviations (δ=−60 percent and δ=−30 percent) result in blurring of the structure details. Specifically, the fine vessels at δ=−60 percent may barely be discerned any more compared with the optimum noise suppression at δ=0 percent, which has been learned or trained, or specified in some other way. For a positive variation of the system parameter (δ=+30 percent and δ=+60 percent), more artifacts appear in the images the larger the deviation from the baseline parameter value.

In the bottom row of images at 100 percent SD, the blurring at δ=−60 percent and the artifacts at δ=+60 percent are less noticeable. This demonstrates the importance that, as regards maintaining the image quality, the ranges for altering the system parameter(s) for noise suppression may be dose-dependent.

For example, it is possible to train a neural network for noise suppression for particular dose values or a defined range of dose values as a prerequisite for the proposed method. Furthermore, it may be possible to alter the selected noise suppression approach with regard to the degree of noise suppression.

Before applying a trained neural network for noise suppression, a test and evaluation phase may be implemented using clinical images or using a mix of phantom acquisitions and clinical images which cover the expected imaging scenarios and the corresponding dose levels. An integral part of this process is, if applicable, implementing a wide variety of alterations of the noise-suppression technique used, (e.g., of the degree of noise suppression), to suit the particular scenes and dose levels in order to cover the possible variations. For each combination of interest, the corresponding image quality may be calculated using suitable image metrics that relate to the general noise suppression performance, for example PSNR (peak signal-to-noise ratio) and to the effect on the structural information, for example SSIM (structural similarity). Instead of using dedicated image-quality metrics or measures of quality, a learning-based approach may also be used which is tailored to the particular task, e.g., identifying variations in the noise suppression performance, the artifacts, the loss of sharpness, and suchlike.

Figure 2:
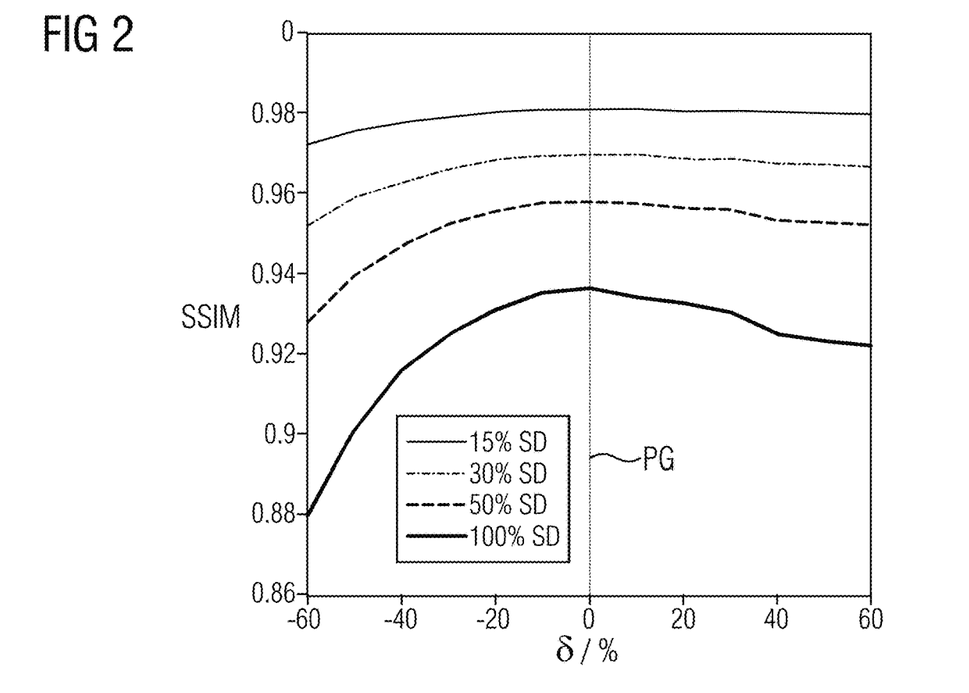
FIG. 2 depicts examples of the noise suppression for different X-ray doses on the basis of SSIM.

FIG. 2 shows an example of the noise suppression performance for X-ray images acquired at various dose levels on the basis of SSIM, with the degree of noise suppression altered over a wide range. The structural similarity SSIM is plotted against the variation δ of the noise suppression parameter for the X-ray doses 15 percent SD, 30 percent SD, 50 percent SD, and 100 percent SD. The lower the X-ray dose, the lower the values of the structural similarity. At the low doses in particular, an associated maximum of the structural similarity is obtained for no deviation (δ=0 percent) from the optimum, (e.g., learned), baseline parameter value. Deviations δ in the positive direction suggest artifacts. These increase as the deviation gets larger, resulting in a corresponding fall in the structural similarity. At an X-ray dose of 100 percent SD, however, the artifacts are barely discernible.

For a negative deviation from the baseline parameter value, (to the left in FIG. 2), the amount of blurring increases as the deviation grows in magnitude. Hence, the structural similarity also falls with the size of the deviation from the baseline parameter value.

On the basis of the determined image quality values for the respective dose levels and alterations, it is possible to determine the variance against the alterations for the respective dose levels, for instance by using a coefficient of variation (CV). This may be done, for example, by regarding the intended degree of noise suppression (for instance in accordance with the training of the algorithm) as the baseline or baseline parameter value and calculating the variation in the image quality within an expanding range about this baseline value.

Figure 3:
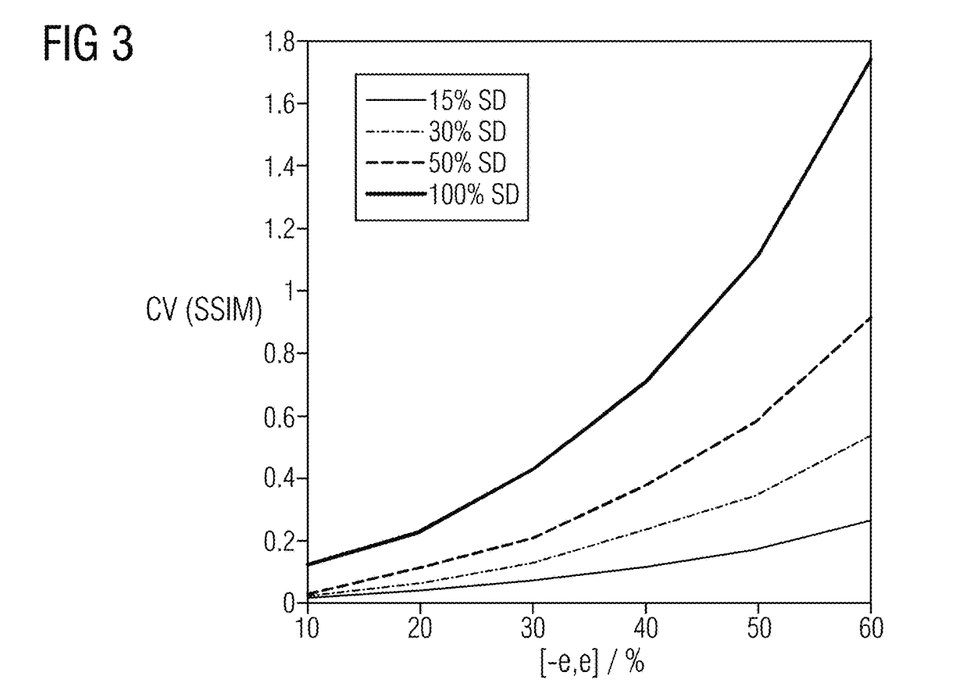
FIG. 3 depicts examples of the coefficients of variation based on SSIM values from FIG. 2.

FIG. 3 shows an example of the resultant CV values. This figure shows the coefficient of variation against an extent of change e for the doses 15 percent SD, 30 percent SD, 50 percent SD, and 100 percent SD. The extent of change e is shown here solely as a magnitude in the positive direction. The extent of change e may also be, for example, the extent of change δ from FIG. 2. It may be seen from FIG. 3 that at high X-ray doses, the coefficient of variation rises only slightly as the change e increases. At low doses, on the other hand, the coefficient of variation CV rises sharply as the change e increases. If applicable, a corresponding figure may also be used that has a positive axis segment, change in a positive direction, and a negative axis segment, change in a negative direction. This is helpful when it is required to determine the maximum values separately for positive/negative values.

A threshold value S1 (see FIG. 4) for defining an acceptable deviation in image quality may be set on the basis of the values calculated according to FIG. 3. This may be done either manually or in an automated manner, where the threshold value S1 may depend on additional information, for example, about the clinical scenario and the potentially acceptable image degradation. For instance, a lower X-ray dose may be used in fluoroscopy. Information that a particular doctor tends to prefer smoother images than is typical, may also be taken into account as additional information, however.

Both options for determining a threshold value or alterable threshold values may be supported by an observer study, or by a trained algorithm that incorporates concepts of visual perception. On the basis of the threshold values, it is possible to determine for each dose level the maximum range of variation about the baseline parameter value, or trained adjustment, for noise suppression (see FIGS. 1 and 2) with regard to image quality, which range satisfies the threshold value condition.

Figure 4:
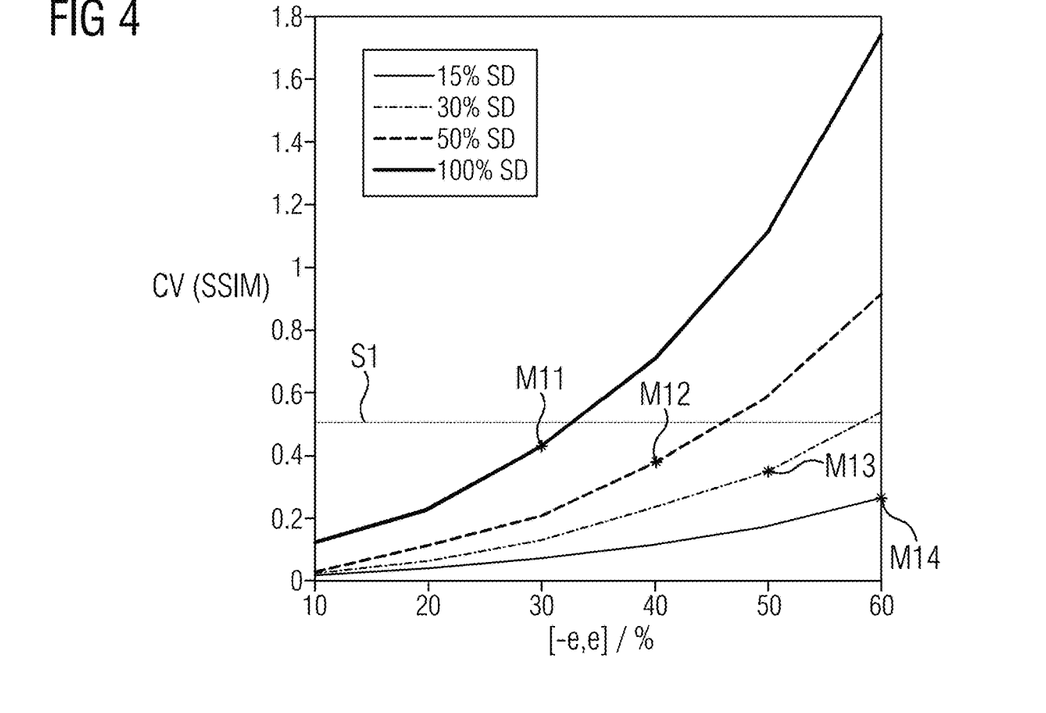
FIG. 4 depicts examples of maximum values from a first threshold with reference to FIG. 3.

FIG. 4 shows an example of setting the threshold value S1, and the resultant maximum values M11, M12, M13, and M14 for each dose level (15 percent SD, 30 percent SD, 50 percent SD, and 100 percent SD). In this case, a threshold value S1 that has a coefficient of variation CV (based on the SSIM) of value 0.5 is defined or determined automatically. For each X-ray dose (15 percent SD, 30 percent SD, 50 percent SD, and 100 percent SD), a corresponding quality function is plotted, which depicts the quality metric (CV in this case) against the magnitude of the parameter variation e. In principle, the points at which these quality functions cross the threshold value S1 may be defined as the maximum values for the parameter change. In the present example, however, the intention is to stop at multiples of 10 percent of the parameter change e at which the threshold value S1 is still just not exceeded. In the specific example of FIG. 4, for the dose 15 percent SD, the value 30 percent is defined as the maximum value M11, (e.g., as the maximum relative amount of change in parameter), because the quality function here still lies below the threshold value S1, whereas at 40 percent it already lies above it. Similarly, the maximum value M12=40 percent is defined for the dose 30 percent SD, the maximum value M13=50 percent for the dose 50 percent SD, and the maximum value M14=60 percent for the dose 100 percent SD.

As a result of applying the threshold value, a corresponding alteration corridor for the parameter alteration in the noise suppression approach about the specified noise-suppression baseline parameter value (for example, obtained by training) may be derived, and subsequently provided to a potential user.

Figure 5:
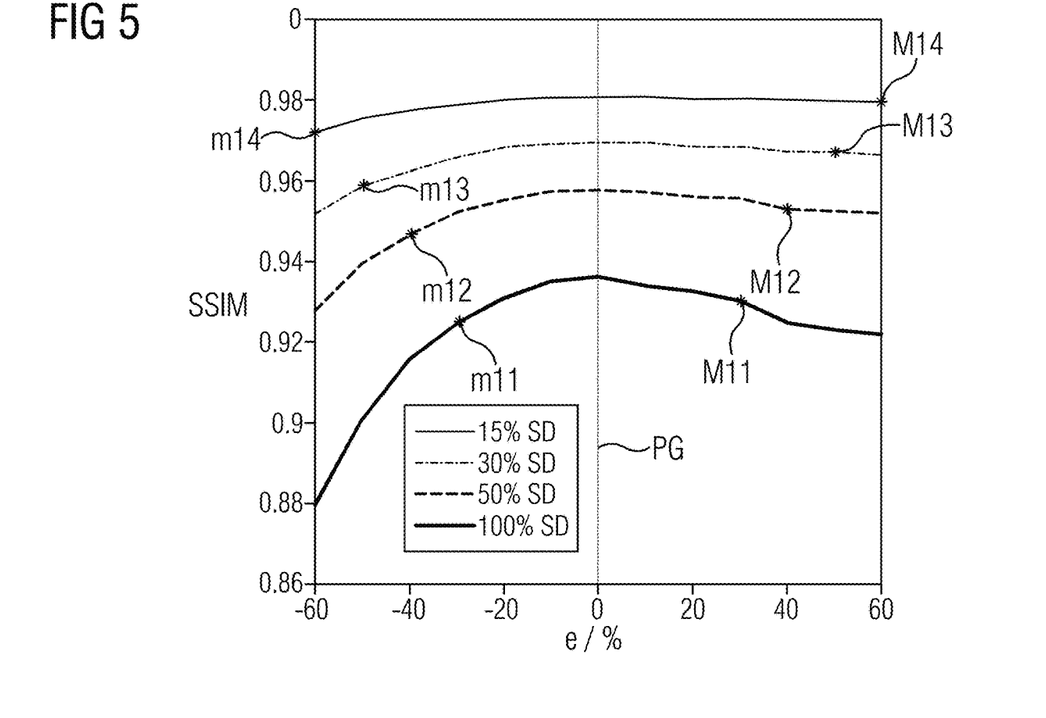
FIG. 5 depicts examples of parameter adjustment ranges according to the maximum values of FIG. 4.

FIG. 5 shows an example of such an alteration corridor of the noise suppressor for each dose level. In this figure, for each dose 15 percent SD, 30 percent SD, 50 percent SD, and 100 percent SD are plotted respective similarity functions against the relative parameter change e (for example, e=δ). As in FIG. 3, the structural similarity SSIM as the ordinate is used as the quality metric or measure of quality. The similarity functions correspond to those in FIG. 3. The similarity curves show the corresponding maximum values M11, M12, M13, and M14, where each maximum value corresponds to the abscissa value, (e.g., M11=30 percent, M12=40 percent, M13=50 percent, and M14=60 percent).

The parameter for noise suppression may also be varied or adjusted in the negative direction. Thus, a corresponding minimum value m11, m12, m13, and m14 is set as the widest possible adjustability. Each of these minimum values is at the same distance from the baseline parameter value PG as the corresponding maximum value. Once again, the minimum values represent simply the corresponding abscissa values, (e.g., m11=−30 percent, m12=−40 percent, m13=−50 percent, and m14=−60 percent). Hence, the noise suppression for a dose of 100 percent SD may be varied between −60 percent and +60 percent without the image quality varying, for instance perceptibly, beyond a certain amount. The parameter may be varied between −50 percent and +50 percent for a dose of 50 percent SD, between −40 percent and +40 percent for a dose of 30 percent SD, and between −30 percent and +30 percent for a dose of 15 percent SD, without perceptible variations in quality.

In one embodiment, the variability of the parameter may be given a fixed dose-dependent limit. A variation from the baseline parameter value beyond the minimum value or maximum value is not possible in this case. In an alternative embodiment, although varying beyond these extreme values is possible, the user receives relevant feedback as soon as the variation goes beyond this extreme value. For example, the user is informed visually, audibly or haptically that the variation is beyond the extreme value. Thus, in this case, the variation is assessed on the basis of the relevant extreme value, and a feedback signal generated accordingly.

Figure 6:
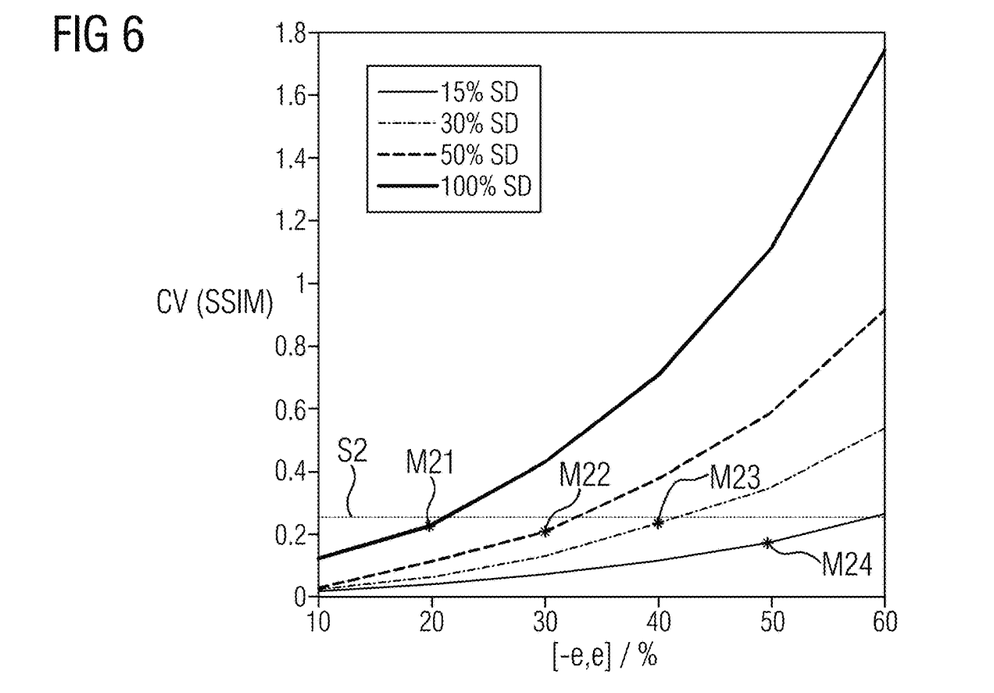
FIG. 6 depicts examples of maximum values according to a second threshold value on the basis of the coefficients of variation of FIG. 3.
Figure 7:
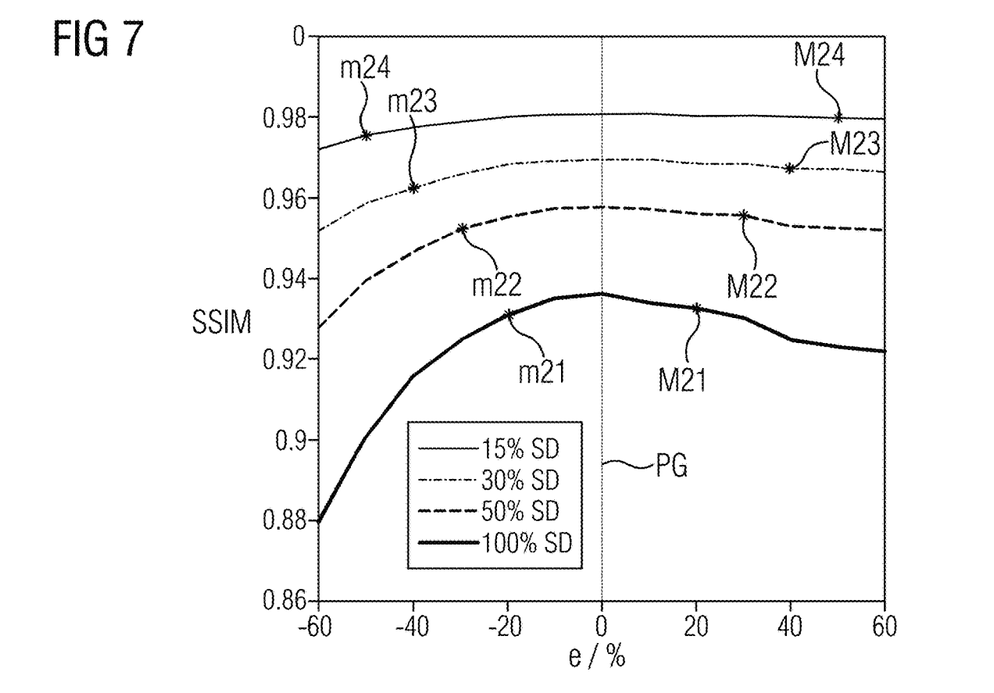
FIG. 7 depicts examples of adjustment ranges for the noise suppression based on the maximum values of FIG. 6.

A further exemplary embodiment is presented in conjunction with FIGS. 6 and 7. FIG. 6 shows the same quality functions as FIG. 4, and FIG. 7 shows the same similarity functions as FIG. 5. In FIG. 6 simply a lower threshold value S2 has been chosen at CV=0.25. Applying the logic of FIG. 4 analogously to FIG. 6 results in the following maximum values: M21=20 percent, M22=30 percent, M23=40 percent and M24=50 percent. Likewise analogous to FIG. 5 are obtained the minimum values, wherein m21=−20 percent, m22=−30 percent, m23=−40 percent, and m24=−50 percent. Thus, as a result of the lower threshold value S2, the noise suppression parameter may be varied without any perceptible change in quality only between −50 percent and +50 percent for the dose 100 percent SD, only between −40 percent and +40 percent for the dose 50 percent SD, only between −30 percent and +30 percent for the dose 30 percent SD, and only between −20 percent and +20 percent for the dose 15 percent SD.

Although the noise suppression is being applied with the option to alter the noise suppression performance, the derived alteration range may be provided to the user as hard boundary conditions, for instance, or as an aid to selecting the degree of noise suppression. Furthermore, such an approach may also be incorporated in a situation-dependent, automatic image alteration concept that makes it possible to provide the user with constant image quality without manual alteration.

Depending on the usage scenario, it is also possible to provide custom adjustment ranges or recommendations for altering the noise suppression performance for particular regions, a particular anatomy, for instance an organ, or structures such as catheters or vessels.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for adjusting a parameter for noise suppression in X-ray imaging, the method comprising:
    providing a baseline parameter value for noise suppression;
    determining, for each X-ray dose of a plurality of X-ray doses, a quality function of a quality metric of an X-ray image in relation to a variation of the parameter for noise suppression with respect to the baseline parameter value;
    setting a maximum value of the variation of the parameter for noise suppression with respect to the baseline parameter value for each quality function, wherein a quality value associated with the particular maximum value in accordance with the particular quality function is less than or equal to a specifiable threshold value; and
    limiting a variability of the parameter for noise suppression according to the X-ray dose up to the corresponding maximum value, or assessing a present variation of the parameter for noise suppression with respect to the corresponding maximum value according to the X-ray dose.

2. The method of claim 1, wherein the quality metric is a structural similarity metric or a noise ratio metric.

3. The method of claim 2, wherein the parameter for noise suppression is a filter parameter of a noise suppression algorithm.

4. The method of claim 3, wherein the plurality of X-ray doses includes a specified standard dose and one or more fractions of the standard dose.

5. The method of claim 4, wherein the one or more fractions of the standard dose is between 10% and 50% of the standard dose.

6. The method of claim 4, wherein the threshold value is specified according to a type of an object to which the X-ray imaging is applied.

7. The method of claim 1, wherein the parameter for noise suppression is a filter parameter of a noise suppression algorithm.

8. The method of claim 1, wherein the plurality of X-ray doses includes a specified standard dose and one or more fractions of the standard dose.

9. The method of claim 8, wherein the one or more fractions of the standard dose is between 10% and 50% of the standard dose.

10. The method of claim 1, wherein the threshold value is specified according to a type of an object to which the X-ray imaging is applied.

11. The method of claim 1, wherein the threshold value is specified in a custom manner.

12. The method of claim 1, wherein each maximum value for limiting an adjustability, or for assessing a present adjustment, of the parameter for noise suppression is used with regard to mathematically positive values, and
    wherein a corresponding minimum value for limiting the adjustability, or for assessing the present adjustment, of the parameter for noise suppression is used with regard to mathematically negative values.

13. The method of claim 12, wherein the corresponding minimum value for a respective maximum value is of a same magnitude.

14. The method of claim 1, wherein the providing of the baseline parameter value for noise suppression is based on computer-implemented learning.

15. A non-transitory computer readable medium comprising a computer program configured to be loaded directly into a memory of a control device of an X-ray imaging apparatus, wherein the computer program, when executed in the control device of the X-ray imaging apparatus, is configured to cause the X-ray imaging apparatus to:
    provide a baseline parameter value for noise suppression;
    determine, for each X-ray dose of a plurality of X-ray doses, a quality function of a quality metric of an X-ray image in relation to a variation of a parameter for noise suppression with respect to the baseline parameter value;
    set a maximum value of the variation of the parameter for noise suppression with respect to the baseline parameter value for each quality function, wherein a quality value associated with the particular maximum value in accordance with the particular quality function is less than or equal to a specifiable threshold value; and
    limit a variability of the parameter for noise suppression according to the X-ray dose up to the corresponding maximum value, or assess a present variation of the parameter for noise suppression with respect to the corresponding maximum value according to the X-ray dose.

16. An X-ray imaging device comprising:
    a control device configured to:
    provide a baseline parameter value for noise suppression;
    determine, for each X-ray dose of a plurality of X-ray doses, a quality function of a quality metric of an X-ray image in relation to a variation of a parameter for noise suppression with respect to the baseline parameter value;
    set a maximum value of the variation of the parameter for noise suppression for each quality function, wherein a quality value associated with the particular maximum value in accordance with the particular quality function is less than or equal to a specifiable threshold value; and
    limit an adjustability of the parameter for noise suppression according to the X-ray dose up to the corresponding maximum value, or assess a present adjustment of the parameter for noise suppression with respect to the corresponding maximum value according to the X-ray dose.

* * * * *